(12) United States Patent
Howarth et al.

(10) Patent No.: US 7,309,503 B2
(45) Date of Patent: Dec. 18, 2007

(54) METHODS FOR THE PREPARATION OF CONCENTRATED AQUEOUS BROMINE SOLUTIONS AND HIGH ACTIVITY BROMINE-CONTAINING SOLIDS

(75) Inventors: Jonathan N. Howarth, Modesto, CA (US); Michael S. Harvey, Modesto, CA (US)

(73) Assignee: Enviro Tech Chemical Services, Inc., Modesto, CA (US)

( * ) Notice: Subject to any disclaimer, the term of this patent is extended or adjusted under 35 U.S.C. 154(b) by 68 days.

(21) Appl. No.: 10/843,030

(22) Filed: May 10, 2004

(65) Prior Publication Data

US 2005/0249825 A1 Nov. 10, 2005

(51) Int. Cl.
| | |
|---|---|
| A61K 33/00 | (2006.01) |
| A61K 33/04 | (2006.01) |
| A61K 33/14 | (2006.01) |
| A61K 33/40 | (2006.01) |
| A01N 59/00 | (2006.01) |
| A01N 59/02 | (2006.01) |
| A01N 59/08 | (2006.01) |
| A01N 39/00 | (2006.01) |

(52) U.S. Cl. .................. 424/723; 424/613; 424/661; 424/663; 424/703; 424/722

(58) Field of Classification Search ............... 424/723, 424/703, 663, 722, 661
See application file for complete search history.

(56) References Cited

U.S. PATENT DOCUMENTS

| | | | |
|---|---|---|---|
| 4,886,915 A | 12/1989 | Favstritsky | |
| 4,966,716 A | 10/1990 | Favstritsky et al. | |
| 5,069,927 A * | 12/1991 | Lawson et al. | ............. 427/491 |
| 5,141,652 A | 8/1992 | Moore, Jr. et al. | |
| 5,683,654 A | 11/1997 | Dallmier et al. | |
| 5,795,487 A | 8/1998 | Dallmier et al. | |
| 5,942,126 A | 8/1999 | Dallmier et al. | |
| 6,007,726 A | 12/1999 | Yang et al. | |
| 6,068,861 A | 5/2000 | Moore, Jr. et al. | |
| 6,123,870 A | 9/2000 | Yang et al. | |
| 6,136,205 A | 10/2000 | Dallmier et al. | |
| 6,156,229 A | 12/2000 | Yang et al. | |
| 6,270,722 B1 | 8/2001 | Yang et al. | |
| 6,287,473 B1 | 9/2001 | Yang et al. | |
| 6,299,909 B1 | 10/2001 | Moore, Jr. et al. | |
| 6,306,441 B1 | 10/2001 | Moore, Jr. et al. | |
| 6,322,822 B1 | 11/2001 | Moore, Jr. et al. | |
| 6,348,219 B1 | 2/2002 | Torres et al. | |
| 6,352,725 B1 | 3/2002 | Torres et al. | |
| 6,375,991 B1 | 4/2002 | Moore, Jr. | |
| 6,423,267 B1 | 7/2002 | Yang et al. | |
| 6,495,169 B1 | 12/2002 | Moore, Jr. et al. | |
| 6,506,418 B1 | 1/2003 | McKinnie et al. | |
| 6,511,682 B1 | 1/2003 | Moore, Jr. et al. | |
| 6,551,624 B2 | 4/2003 | Moore, Jr. | |
| 6,652,889 B2 | 11/2003 | Moore, Jr. et al. | |
| 6,660,307 B2 | 12/2003 | Zolotarsky et al. | |
| 6,669,904 B1 | 12/2003 | Yang et al. | |
| 2004/0022874 A1* | 2/2004 | Nalepa et al. | ............... 424/723 |
| 2004/0262239 A1* | 12/2004 | Howarth et al. | ............. 210/754 |

FOREIGN PATENT DOCUMENTS

| | | |
|---|---|---|
| WO | WO 03/093171 A1 | 11/2003 |
| WO | WO 2004/039159 A1 | 5/2004 |
| WO | WO 2006/029354 A1 | 3/2006 |

* cited by examiner

*Primary Examiner*—Johann Ritter
*Assistant Examiner*—Ernst V Arnold
(74) *Attorney, Agent, or Firm*—Audrey A. Millemann; Weintraub Genshlea et al.

(57) ABSTRACT

The invention includes convenient methods of preparing: (1) highly concentrated liquid bromine-containing biocidal solutions, (2) highly concentrated mixed halogen liquid bromine and chlorine-containing biocidal solutions, and (3) high-activity bromine-containing biocidal solids, all having excellent physical and chemical stability. One method yields solutions that have concentrations of bromine in excess of 18% as $Br_2$ (8% as $Cl_2$) in which the mole ratio of hydroxide ion to hydrogen ion source is at least 1.9:1. Another method employs elemental bromine in conjunction with a solid organic or inorganic halogenating agent to yield halogen solutions at concentrations greater than 22.9% as $Br_2$ (10.2% as $Cl_2$). This method can be performed under conditions that exceed the solubility of the active ingredient such that it crystallizes and is recovered as a hydrated or anhydrous salt in good yield.

17 Claims, No Drawings

METHODS FOR THE PREPARATION OF CONCENTRATED AQUEOUS BROMINE SOLUTIONS AND HIGH ACTIVITY BROMINE-CONTAINING SOLIDS

BACKGROUND OF THE INVENTION

1. Field of the Invention

The invention relates to methods for the preparation of concentrated aqueous bromine solutions and high activity bromine-containing solids using elemental bromine or bromine chloride. The products are used as microbiocides in water treatment.

2. Description of the Related Art

Single feed bromine biocide solutions are available from a number of sources and many methods to manufacture these products have been reported. These methods fit into two general categories: those that employ sodium hypochlorite solutions with a source of bromide ion, and those that employ elemental bromine or bromine chloride.

The prior art methods that use a sodium hypochlorite solution with a source of bromide ion yield a stabilized solution with a maximum active ingredient concentration of 14% as $Br_2$ (6.4% as $Cl_2$). For example, U.S. Pat. Nos. 5,683,654, 5,795,487, 5,942,126, and 6,136,205 all describe a method to manufacture a single feed, liquid bromine biocide by mixing an aqueous hypochlorite solution with bromide ion sources followed by introduction of a stabilizer agent. The method requires a complex two-vessel reaction. In the first step, NaBr and NaOCl solutions were mixed and sufficient time was allowed to permit the formation of a sodium hypobromite (NaOBr) solution. In the second step, this was then introduced to a solution of the stabilizer agent maintained at 50° C. The disadvantage of this method is that the concentration of the stabilized bromine product is limited by the concentration of NaOCl bleach that is commercially available. In fact, despite using the highest strength grade of industrial NaOCl bleach, the bromine content of the resulting stabilized liquid bromine solution was only about 14% as $Br_2$ (6.4% as $Cl_2$).

The prior art method that uses elemental bromine or bromine chloride yields a solution with a higher active ingredient concentration than the method that uses a sodium hypochlorite solution with a source of bromide ion. Moore, et. al. overcame the complexity of the two-vessel reaction in U.S. Pat. Nos. 6,068,861, 6,495,169, and 6,322,822 and disclosed a single-vessel reaction in which bromine or bromine chloride was added to a halogen stabilizer solution under conditions of pH control. These three patents disclosed two solutions (described in examples 4 and 5 of the '169 and '861 patents) having an active ingredient concentration of at least 19.6% as $Br_2$ (8.7% as $Cl_2$). However, no elevated temperature, chemical, or physical stability data was reported for either solution, and the present inventors have concluded that these two solutions are either unstable or have inferior stability.

The solution disclosed in example 5 of the '169 and '861 patents was reported to contain up to 26.7% as $Br_2$ (11.5% as $Cl_2$), but it had a pH of 7.0 and possessed a distinct bromine odor. It is well known that these types of solutions undergo acid-generating decomposition reactions upon storage. Thus, as the pH dropped below 7.0, highly toxic bromine vapors would have fumed from the solution and appeared as an orange/brown gas in the headspace of the container. This demonstrates that the solution of example 5 was physically unstable, and therefore, unacceptable for its intended use. The solution disclosed in example 4 of the '169 and '861 patents was reported to contain 19.6% as $Br_2$ (8.7% as $Cl_2$), with a pH of 13.0 and no odor of bromine. However, it has been concluded, as will be shown herein, that this solution has inferior chemical and physical stability.

Moreover, when the method using elemental bromine or bromine chloride was scaled up, as disclosed in U.S. Pat. Nos. 6,306,441, 6,352,725 and 6,348,219, the hypothetical maximum active ingredient concentration was reported to be 18% as $Br_2$ (8% as $Cl_2$). Subsequently, in U.S. Pat. Nos. 6,506,418, 6,511,682, and 6,652,889, Moore, et. al. reduced this ceiling even further to 14.5%-16% as $Br_2$ (6.4-7.1% as $Cl_2$) and required the adjustment of the pH to greater than 10 in order to produce a useful product. The '418 patent, in example 2, described the maximum strength solution as one containing 14.8% as $Br_2$ (6.59% as $Cl_2$).

Published application WO 03/093171 disclosed a method for preparing a stabilized bromine solution with a halogen content higher than any previously reported solution prepared from hypochlorite and sodium bromide. Example 1 of WO 03/093171 described a cumbersome multi-step method. In the first step, an unstabilized solution of sodium hypobromite was made by adding elemental bromine to a sodium hydroxide solution and allowing the mixture to react. Introducing a solution of sodium sulfamate prepared by reacting sulfamic acid with a solution of sodium hydroxide followed this. The resulting product was determined to possess a halogen content of 19.6% as $Br_2$ (8.7% as $Cl_2$). Example 4 of the same application disclosed an even more complex multi-step method for preparing a solution reported to have a halogen concentration of 21.6% as $Br_2$ (9.6% as $Cl_2$). However, it appears to the present inventors that this concentration is erroneous because the maximum concentration that can be obtained from the stated quantities of the components (even assuming a 100% yield in every step), is calculated to be 19.7% as $Br_2$ (8.7% as $Cl_2$). In actuality, the concentration that was obtained was probably substantially less than 19.7% as $Br_2$ (8.7% as $Cl_2$), because it is well-known that the first step cannot proceed with a 100% yield.

The prior art also discloses that other methods also fail to yield satisfactory products in terms of higher active ingredient concentration, physical stability, and reaction efficiency. For example, Moore described a method in U.S. Pat. Nos. 6,375,991 and 6,551,624 that used gaseous chlorine and a source of bromide ion. The reaction conditions sought the preparation of a solution possessing a theoretical bromine content of 16.8% as $Br_2$ (7.45% as $Cl_2$), but the actual amount reported was 10.4% as $Br_2$ (4.6% as $Cl_2$), corresponding to a yield of 66%. In addition, the resulting solution was stated to be physically unstable as sodium chloride salt precipitated from the aqueous phase towards the end of the reaction. Similarly, Yang, et. al. reported an identical phenomenon in U.S. Pat. No. 6,270,722.

Thus, the prior art teaches that convenient, efficient, scalable methods for preparing chemically and physically stable, liquid bromine-containing solutions will result in a product with an active ingredient concentration of 18% as $Br_2$ (8% as $Cl_2$) at the maximum.

Liquid bromine products that contain a higher level of active ingredient have significant economic advantages over more dilute products because a smaller amount of a more concentrated product can be used to achieve the equivalent dose of a weaker product. Also, more concentrated products need to be replaced less frequently than dilute products, and have reduced packaging, storage, and transportation costs per unit weight of active ingredient.

To be commercially viable, products with a high level of active ingredient must have two attributes. First, they must be chemically stable, i.e. they should maintain high activity for extended periods of time and not decompose quickly. Second, they must be physically stable, i.e. they must not emit dangerous fumes or precipitate or crystallize into solid salts that could plug pipe work and make the feeding of liquid materials grind to a halt.

Therefore, a need exists for methods of manufacturing liquid biocidal bromine solutions of enhanced chemical and physical stability that have a concentration of active ingredient greater than 18% as $Br_2$ (8% as $Cl_2$) and that conveniently employ elemental bromine or bromine chloride and a solution of sodium sulfamate. This invention addresses that need.

There is also a need for a method of producing a solid high-activity bromine-containing biocidal composition that is stable and fast dissolving. There are several solid, high-activity bromine-releasing compounds that are sold commercially as biocidal products. They are generally available as heterocyclic organic compounds to which an oxidizing bromine atom is covalently bonded to a nitrogen atom on the ring. Examples include N,N' bromochloro-5,5-dimethylhydantoin, 1,3-dibromo-5,5-dimethylhydantoin, and mixtures of these compounds with various other components. In water, these materials hydrolyze to release hypobromous acid, which is the biocidal agent. However, a major limitation of these solid compounds is that they are only sparingly soluble in water. Indeed, N,N' bromochloro-5,5-dimethylhydantoin has a water solubility of only 0.1% at 20° C. As a result, bromine is released very slowly from these products as they dissolve. This is a significant disadvantage when the water requires treatment with a high, rapid dose of biocidal bromine, for example, in shock and slug dosing procedures. The low solubility of these products also precludes application where there is insufficient water available to dissolve enough of the solid to deliver a biocidally-effective dose. This invention addresses those needs.

SUMMARY OF THE INVENTION

The present invention is directed to convenient methods of preparing: (1) highly concentrated liquid bromine-containing solutions, (2) highly concentrated mixed halogen liquid bromine and chlorine-containing solutions, and (3) high-activity bromine-containing solids, all having excellent physical and chemical stability.

Contrary to the teachings of the prior art, the present invention discloses methods in which elemental bromine or bromine chloride is introduced to a sulfamate solution to yield a final solution having a concentration of active ingredient in excess of 18% as $Br_2$ (8% as $Cl_2$). The methods of the present invention also yield a final solution having a mole ratio of hydroxide ion to hydrogen ion source (e.g. sulfamic acid plus $Br_2$ or BrCl) of greater than 1.62:1. In this context, the hydrogen ion source is defined as being the sum of the reagents that dissociate into strong acids in water, e.g. sulfamic acid or other acidic stabilizer plus $Br_2$ or BrCl. The present inventors have discovered that calculating this mole ratio is a more accurate way of determining the amount of hydroxide ion to use to obtain a final solution of high concentration, than the methods used by the prior art. The prior art methods use a pH measurement, and teach that the amount of hydroxide ion that should be added is the amount necessary to raise the pH to about 13. It is believed, however, that this method is unreliable because under conditions of high pH, glass electrodes suffer a phenomenon known as "alkaline error". The low activity of $H^+$ ions in solution means that the electrode responds instead to the much higher concentration of $Na^+$ ions, resulting in a pH measurement that is artificially low.

The methods of the present invention do not rely on a pH measurement, but rely instead on the mole ratio of hydroxide ion to hydrogen ion source. Utilizing this approach, it was unexpectedly discovered that this ratio is of critical importance to the chemical and physical stability of the finished product. Nowhere in the prior art is this mole ratio discussed. However, the present inventors have calculated the mole ratio for several of the solutions produced by introducing elemental bromine or BrCl to a solution of sodium sulfamate that have been disclosed in the prior art and found them all to be less than or equal to 1.62:1. For instance, in example 5 of U.S. Pat. No. 6,068,861 it was calculated that the method employed a hydroxide ion to hydrogen ion source (sulfamic acid plus $Br_2$) mole ratio of 1:1 and obtained a product that had a measured pH of 7. Example 4 of the same patent described a solution containing 19.6% as $Br_2$ (8.7% as $Cl_2$) that utilized a hydroxide ion to hydrogen ion source (sulfamic acid plus $Br_2$) mole ratio of 1.62:1. This solution had a measured pH of 13.0. No elevated temperature, chemical, or physical stability data was reported for either of these solutions. Example 2 of U.S. Pat. No. 6,506,418 described a method involving the addition of both $Br_2$ and $Cl_2$ to a solution of sodium sulfamate to a maximum strength solution of 14.8% as $Br_2$ (6.59% as $Cl_2$). Again, this utilized a hydroxide ion to hydrogen ion source (sulfamic acid plus $Br_2$ plus $Cl_2$) mole ratio of 1.62:1. Thus, solutions produced using the introduction of $Br_2$ or BrCl to a solution of sodium sulfamate that have a mole ratio of hydroxide ion to hydrogen ion source of greater than 1.62:1 have not been previously reported. As will be subsequently demonstrated, such solutions display dramatically enhanced chemical and physical stability over those in which the mole ratio is less than or equal to 1.62:1.

The products of the methods of this invention are sources of oxidizing bromine that are useful for microbiological control in aqueous systems. This is generally achieved by introducing the products into water requiring microbiological control in an amount sufficient to be biocidally effective. Applications include industrial water systems such as recirculating cooling water, once-through cooling water, air washer systems, decorative fountains, oil field injection water, oil well completion fluids, municipal and industrial wastewater, brewery pasteurizing water, hydrostatic sterilizer cooling water, pulp and paper processing water, and agricultural irrigation water. Other applications include residential water systems where the home consumer can apply the compositions in aqueous systems where microbiological control is necessary, such as pool and spa water, kitchen and bathroom rinses, toilet bowl rinses, and mold and fungus sprays for inside and outside the home.

The first embodiment of the invention is a method for preparing highly concentrated liquid bromine-containing solutions using elemental bromine or bromine chloride. The method yields solutions that have concentrations of bromine in excess of 18% as $Br_2$ (8% as $Cl_2$) and possess a hydroxide ion to hydrogen ion source (e.g. sulfamic acid plus $Br_2$ or BRCl) mole ratio of at least 1.9:1. These solutions are chemically and physically stable. They resist precipitation of inert salts, do not emit highly toxic bromine fumes, and yet display excellent retention of the active ingredient upon storage. Using the method of the first embodiment, solutions at concentrations of at least 19.7% as $Br_2$ (8.8% as $Cl_2$) can be prepared.

The second embodiment of the invention is a method for preparing highly concentrated liquid bromine-containing solutions using elemental bromine in conjunction with a solid organic or inorganic halogenating agent. The method yields solutions that are chemically and physically stable and possess concentrations of bromine of at least 11.25% as $Br_2$ (5% as $Cl_2$). Using this method, it is possible to prepare such solutions at concentrations greater than 22.9% as $Br_2$ (10.2% as $Cl_2$). Physical and chemical stabilization of the solutions is achieved using a hydroxide ion to hydrogen ion source (e.g. sulfamic acid plus $Br_2$) mole ratio of at least 1.9:1.

The third embodiment of the invention is a method for preparing highly concentrated mixed halogen solutions that contain both bromine and chlorine. The method utilizes elemental bromine in conjunction with a solid organic or inorganic chlorinating agent. The method yields solutions that have excellent chemical and physical stability, and possess total halogen concentrations of at least 11.25% when expressed as $Br_2$ (5% when expressed as $Cl_2$). Using this method, it is possible to prepare such solutions having concentrations of total halogen that are greater than 22.7% when expressed as $Br_2$ (10.1% when expressed as $Cl_2$). Physical and chemical stabilization of the solutions is achieved using a hydroxide ion to hydrogen ion source (e.g. sulfamic acid plus $Br_2$) mole ratio of at least 1.9:1.

The fourth embodiment of the invention is a method for preparing solid bromine-containing compositions. This method utilizes elemental bromine in conjunction with a solid organic or inorganic halogenating agent to prepare three end products. The first is a saturated solution of the alkali metal or earth alkali metal salt of hydrated N-bromosulfamate. The second and third are the solid alkali metal or earth alkali metal salt of hydrated N-bromosulfamate and the solid alkali metal or earth alkali metal salt of anhydrous N-bromosulfamate, respectively. These end products were previously disclosed in U.S. patent application Ser. No. 10/609,280, filed by the present inventors on Jun. 27, 2003.

A very surprising aspect of the method of the first embodiment is that physically and chemically stable, liquid bromine-containing solutions prepared using elemental $Br_2$ or BrCl do not have a ceiling on their concentration of 18% as $Br_2$ (8% as $Cl_2$), as the prior art suggests. The stabilization is accomplished by employing a hydroxide ion to hydrogen ion source (e.g. sulfamic acid plus $Br_2$ or BRCl) mole ratio of at least 1.9:1.

A major benefit of the methods of the second and third embodiments is that all of the Br moieties introduced to the reactor as elemental bromine materialize as active bromine in the final product. None of the Br moieties are wasted as by-product inactive bromide ion salts. The solid organic or inorganic halogenating agents serve to reactivate the bromide ions to ensure that both bromine atoms of the $Br_2$ molecule are utilized as active forms in the products.

A noteworthy feature of the method of the second embodiment is that it provides stable, aqueous bromine-containing compositions that contain significantly lower amounts of contaminant halide ion salts than the methods of the prior art. The method of the second embodiment results in an all-bromine liquid composition with a far lower level of halide ion contaminant per mole of active bromine than is possible using alternative methods. Thus, this method yields a product in which halide ion-induced physical and chemical destabilization is significantly reduced. Assuming a 100% reaction yield, Table I compares the ratio of inactive, soluble halide ion ($X^-$) to active bromine in the final product when various alternative reagents are used.

TABLE I

| Reagent | Moles dissolved $X^-$ ion/mole stabilized active bromine |
|---|---|
| $Br_2$ | 1 |
| BrCl | 1 |
| $Br_2 + Cl_2$ | 1 |
| NaOCl + NaBr | 2 |
| $Cl_2$ + NaBr | 2 |
| Second embodiment | 0.5 |

The data in Table I helps explain why the method of the second embodiment yields physically stable, highly concentrated all-bromine liquid formulations that are not possible by any other route. Because the aqueous phase is far lower in contaminant halide ion salts, it is able to support the dissolution of higher levels of active ingredient without "salting out".

A noteworthy feature of the method of the third embodiment is that it provides stable, aqueous mixed halogen bromine and chlorine-containing compositions that contain significantly lower amounts of contaminant halide ion salts than the methods of the prior art which only yield all-bromine products. The method of the third embodiment results in a mixed halogen liquid composition with a far lower level of halide ion contaminant per mole of active halogen. Thus, this method yields a product in which halide ion-induced physical and chemical destabilization is significantly reduced. Assuming a 100% reaction yield, Table II compares the ratio of inactive, soluble halide ion ($X^-$) to active halogen in the final product when various alternative reagents are used.

TABLE II

| Reagent | Moles dissolved $X^-$ ion/mole stabilized active bromine |
|---|---|
| $Br_2$ | 1 |
| BrCl | 1 |
| $Br_2 + Cl_2$ | 1 |
| NaOCl + NaBr | 2 |
| $Cl_2$ + NaBr | 2 |
| Third embodiment | <0.5* |

*the exact amount depends on the desired mole ratio of bromine:chlorine in the finished product The data in Table II helps explain why the method of the third embodiment yields physically stable, highly concentrated mixed halogen liquid formulations that are not possible by any other route. Because the aqueous phase is far lower in contaminant halide ion salts, it is able to support the dissolution of higher levels of active ingredient without "salting out".

A significant advantage of the methods of the second and third embodiments is that they use solid halogenating agents. Because solid halogenating agents are devoid of water, the halogen content of the finished compositions is not diluted as would be the case if hypochlorite solutions were used to accomplish the same chemical reaction. Further, these solid halogenating agents are generally high in available halogen and do not contain large amounts of extraneous salts or inactive ingredients that enter the finished product (see, for example, WO 03/093171). Hence, the compositions that are obtained using solid halogenating agents possess lower levels of water, as well as lower levels of dissolved salts or other extraneous materials, which would otherwise dilute the available halogen content of the product and adversely impact its chemical and physical stability.

Another remarkable benefit of this invention is that the methods of the second and third embodiments make possible the formation of highly concentrated liquid bromine-containing compositions employing methods that generate no solid wastes. Thus, using solid organic halogenating reagents such as trichloroisocyanuric acid (TCCA) (also known as trichloro-s-triazinetrione), sodium dichlorisocyanurate (NaDCC) (also known as sodium dichloro-s-triazinetrione), sodium dichlorisocyanurate dihydrate (NaDCC.2H$_2$O) (also known as sodium dichloro-s-triazinetrione dihydrate), potassium dichloroisocyanurate, or dichloroisocyanuric acid, the by-product of the halogenation reaction is cyanuric acid (CA). This is insoluble in the reaction medium and precipitates in a solid form. Upon filtration and washing, highly purified CA wetcake is recovered. This can be recycled to other methods to make additional quantities of TCCA, NaDCC, or NaDCC.2H$_2$O that can be used in the methods of this invention.

A notable discovery of this invention is that the method of the fourth embodiment can be performed under conditions that exceed the solubility of the hydrated alkali metal or earth alkali metal salt of N-bromosulfamate, and further, that the resulting solid can be crystallized and recovered in good yield.

DETAILED DESCRIPTION OF THE INVENTION

The First Embodiment

The first embodiment is a method for preparing highly concentrated liquid bromine-containing solutions using Br$_2$ or BrCl. Table III lists the basic components of solutions prepared using Br$_2$ or BrCl that contain an active ingredient of 18.1% as Br$_2$ (8.04% as Cl$_2$) and which possess a hydroxide ion to hydrogen ion source (sulfamic acid plus Br$_2$ or BrCl) mole ratio of 2.3:1. Higher concentrations than this are prepared by employing more elemental Br$_2$ or BrCl at the expense of sulfamic acid, water, or 50% sodium hydroxide solution provided the hydroxide ion to hydrogen ion source mole ratio does not drop below 1.9:1. The golden colored solutions that are produced using this method contain 27-39% or 35-52% more active bromine than solutions that are available commercially, respectively, depending on whether Br$_2$ or BrCl is used.

The method of this embodiment includes the following steps. Steps (a), (b), (c), and (d) may be performed sequentially or as otherwise set forth below. Steps (a) and (b) may be performed simultaneously, followed by the remaining steps. Steps (b) and (d) may be combined so that all of the alkaline source is added in step (b). If performed, step (d) may be conducted at the same time as step (c).

a. Dispersing solid sulfamic acid in an aqueous phase.

Sulfamic acid displays moderate solubility in water (14.7 g/100 g at 0° C.). When the amount of sulfamic acid added to water exceeds the solubility limit at any given temperature, some of the solid remains undissolved. Upon stirring the mixture, the sulfamic acid solids are dispersed in the aqueous phase. As indicated in Table III, the amount of water used to disperse the sulfamic acid depends on whether elemental bromine or bromine chloride is used. Preferably, a slurry of between about 25% and about 75% solid sulfamic acid in water is employed, with about 30% to about 40% being the most preferred range.

b. Forming a solution of the alkali metal or earth alkali metal salt of sulfamic acid in the aqueous phase.

To the stirred dispersion of solid sulfamic acid in water is added an alkaline source in order to form a solution of the alkali metal or earth alkali metal salt of sulfamic acid. Any alkaline source may be employed. Examples include, but are not limited to, alkali metal or earth alkali metal carbonates, bicarbonates, oxides, and hydroxides. When solutions are preferred, sodium hydroxide or potassium hydroxide solutions may be used, alone or in combination with each other. A particularly preferred alkaline source is 50% NaOH solution. To prevent storage problems in cold climates, the 50% NaOH solution may be diluted with water and used. The sodium hydroxide solution is introduced to the reaction medium slowly, with stirring and cooling, such that the temperature preferably does not exceed about 85° F. The amount of 50% NaOH solution employed should preferably be at least sufficient to fully neutralize the sulfamic acid and form sodium sulfamate according to equation (1).

$$NH_2SO_3H + NaOH \rightarrow [NH_2SO_3^-][Na^+] + H_2O \quad (1)$$

Preferably, a molar excess of 50% NaOH is utilized relative to the amount of sulfamic acid. The mole ratio of hydroxide ion to sulfamic acid is preferably between about 2:1 and about 4:1, most preferably between about 2:1 and about 3:1.

If available, solid alkali metal salts of sulfamic acid may be used. In these circumstances, it is only necessary to dissolve the salts in water to make a solution. Preferably, an additional quantity of 50% NaOH is then utilized. The mole ratio of hydroxide ion to alkali metal salt of sulfamic acid is preferably between about 1:1 and about 3:1, most preferably between about 1:1 and about 2:1.

c. Introducing bromine chloride or elemental bromine.

The amount of bromine chloride or elemental bromine added depends on the amount of sulfamic acid originally present. A mole ratio of about 0.75:1 to about 1.5:1 sulfamic acid to bromine chloride or elemental bromine is advantageous to the stability of the final product, with about 0.95:1 to about 1.2:1 being the most preferred mole ratio range.

Table III shows the quantities of elemental bromine or bromine chloride needed to introduce to the reaction medium in order for the resulting solution to have an active ingredient concentration of 18.1% as Br$_2$ (8.04% as Cl$_2$). Higher concentrations than this are prepared by employing more elemental bromine or bromine chloride at the expense of sulfamic acid, water, or 50% NaOH solution provided the hydroxide ion to hydrogen ion source (sulfamic acid plus Br$_2$ or BrCl) mole ratio does not drop below about 1.9:1.

TABLE III

|  | Br$_2$ (Wt %) | BrCl (Wt %) |
|---|---|---|
| Br$_2$ | 18.1 | — |
| BrCl | — | 13.0 |
| Sulfamic Acid | 13.2 | 13.2 |
| 50% NaOH | 45.8 | 45.8 |
| Water | 22.9 | 28.0 |

The bromine chloride or elemental bromine is dropped into the reaction medium from above the surface, or it may be introduced subsurface via a dip tube. When the latter is preferred, the dip tube should be positioned so that the BrCl or Br$_2$ is introduced to an area of high turbulence, e.g. near the tip of a rotating agitator blade so that it is well dispersed into the reaction medium. For both supersurface and subsurface addition methods, the BrCl or $Br_2$ is added with sufficient mixing and at a rate to avoid significant phase separation and pooling of the materials at the bottom of the reactor.

With adequate mixing and dispersion, the BrCl or $Br_2$ introduced to the reactor containing the solution of sodium hydroxide and sodium sulfamate hydrolyzes readily according to reaction (2).

$$Br—X+H_2O \rightarrow HOBr+HX \quad (2)$$

X=Br or Cl

The hypobromous acid formed reacts with sodium sulfamate to form sodium N-bromosulfamate according to reaction (3).

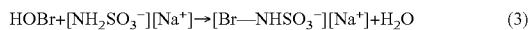

$$HOBr+[NH_2SO_3^-][Na^+] \rightarrow [Br—NHSO_3^-][Na^+]+H_2O \quad (3)$$

The HBr or HCl that is generated in reaction (2) immediately undergoes an acid-base neutralization reaction with the excess sodium hydroxide present in solution as illustrated by reaction (4).

$$HX+NaOH \rightarrow Na—X+H_2O \quad (4)$$

X=Br or Cl

This is a strongly exothermic reaction, so the reaction medium is cooled, preferably to below about 85° F., to suppress the degradation of sodium N-bromosulfamate formed in reaction (3).

d. Adding an alkaline source to the reaction medium such that if the alkaline source is a hydroxide ion salt, the overall mole ratio of hydroxide ion to sulfamic acid is between about 3:1 and about 5:1, preferably between about 4:1 and about 5:1.

If desired, steps (b) and (d) may be combined so that all of the hydroxide ion charge is added in step (b), and the method concludes with step (c).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions can be used, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed about 85° F.

When the sodium salt of sulfamic acid is employed, and when the alkaline source is 50% sodium hydroxide, the overall mole ratio of hydroxide ion to sodium sulfamate is preferably between about 2:1 and about 4:1, most preferably between about 3:1 and about 4:1.

EXAMPLE 1

Deionized water (52.5 ml) was introduced to a four-necked round bottom flask and solid sulfamic acid (24.9 g) was added. The slurry was stirred and 50% NaOH (44.6 g) was slowly added as the flask was chilled in an ice bath to keep the temperature of the flask contents below about 85° F. Using a dropping funnel, elemental bromine (41.2 g) was dispensed at a rate of about one drop per second to the reaction medium, also with stirring and cooling to maintain a reaction temperature below about 66° F. After the addition was complete, 50% NaOH (37.6 g) was slowly added from the dropping funnel as the reaction flask was stirred and cooled. Iodometric titration of the resultant golden yellow solution yielded a bromine content of 19.8% as $Br_2$ (8.8% as $Cl_2$) that corresponded to a yield of 96.6% (based on the bromine charge). The solution possessed a hydroxide ion to hydrogen ion source (sulfamic acid plus $Br_2$) mole ratio of 2.0:1.

(PROSPECTIVE) EXAMPLE 2

From the data in Table III, it is apparent that solutions prepared using BrCl will always contain more water than equivalent solutions prepared using elemental bromine. This is because BrCl has a molecular weight of 115.4 compared to 159.8 for elemental bromine. Therefore, because of their higher relative water content, solutions prepared using BrCl should be able to support the dissolution of even higher levels of active ingredient than their counterparts prepared using elemental bromine. In this prospective example, the $Br_2$ that was used in Example 1 is replaced with a molar equivalent amount of BrCl.

Deionized water (52.5 ml) is introduced to a four-necked round bottom flask and solid sulfamic acid (24.9 g) is added. The slurry is stirred and 50% NaOH (44.6 g) is slowly added as the flask was chilled in an ice bath to keep the temperature of the flask contents at below 85° F. Using a dropping funnel, bromine chloride (29.7 g) is dispensed at a rate of about one drop per second to the reaction medium, also with stirring and cooling to maintain a reaction temperature below about 66° F. When the bromine chloride addition is complete, the pH of the reaction medium is approximately 10.26. Then, 50% NaOH (37.6 g) is slowly added from the dropping funnel as the reaction flask is stirred and cooled. Assuming a yield of 96.6% (based on the bromine chloride charge), the resultant solution would have a bromine content of 21% as $Br_2$ (9.3% as $Cl_2$).

EXAMPLE 3

For the purposes of comparative elevated temperature stability testing, the reaction of Example 1 was repeated, except that a hydroxide ion to hydrogen ion source (sulfamic acid plus $Br_2$) mole ratio of 1.69:1 was employed.

Deionized water (69.1 ml) was introduced to a four-necked round bottom flask and solid sulfamic acid (24.6 g) was added. The slurry was stirred and 50% NaOH (44.6 g) was slowly added as the flask was chilled in an ice bath to keep the temperature of the flask contents below about 85° F. Using a dropping funnel, elemental bromine (41.2 g) was dispensed at a rate of about one drop per second to the reaction medium, also with stirring and cooling to maintain a reaction temperature below about 66° F. After the addition was complete, 50% NaOH (24.5 g) was slowly added from the dropping funnel as the reaction flask was stirred and cooled. Iodometric titration of the resultant golden yellow solution yielded a bromine content of 19.6% as $Br_2$ (8.7% as $Cl_2$) that corresponded to a yield of 97% (based on the bromine charge).

Samples of the solutions prepared in Examples 1 and 3 were poured into capped plastic containers and placed in an oven held at 125° F. The amount of active ingredient remaining in the formulations was monitored as a function of time. The physical stability was established by visual observation of whether any solids precipitated from solution over the same period. Table IV shows the results.

TABLE IV

| | Example 1 Mole ratio OH⁻:H⁺ source 2.0:1 | | | Example 3 Mole ratio OH⁻:H⁺ source 1.69:1 | | |
|---|---|---|---|---|---|---|
| Time/days | Wt % $Br_2$ | % $Br_2$ remaining | Solids Formed | Wt % $Br_2$ | % $Br_2$ remaining | Solids Formed |
| 0 | 19.8 | 100 | No | 19.6 | 100 | No |
| 4 | — | — | — | 14.8 | 75.6 | No |
| 5 | — | — | — | 13.7 | 70.0 | No |
| 6 | — | — | — | 12.8 | 65.3 | No |
| 7 | — | — | — | 11.7 | 59.7 | No |
| 10 | — | — | — | 10.3 | 52.5 | No |
| 11 | — | — | — | 9.9 | 50.5 | No |
| 12 | — | — | — | 9.0 | 45.9 | No |
| 13 | — | — | — | 7.0 | 35.7 | Slight |
| 14 | 17.3 | 87.4 | No | 2.0 | 10.2 | Slight |
| 31 | 15.1 | 76.2 | Slight | — | — | — |

It can be seen that the hydroxide ion to hydrogen ion source mole ratio has a dramatic effect on both the chemical and physical stability of solutions prepared with almost identical amounts of $Br_2$. The solution of Example 3, with the lower mole ratio, suffered a steady loss of $Br_2$ daily before rapidly declining at day 14 to possess only 10.3% of the original amount of $Br_2$. This was accompanied by a loss in physical stability as indicated by the precipitation of solids from the solution. In stark contrast, the solution of Example 1, with the higher mole ratio, retained 87.4% of its original $Br_2$ content after the same time period, and had not experienced any signs of physical instability. Even after 31 days, the Example 1 solution still retained 76.2% of its original activity, and only then began to exhibit solids precipitation.

The Second Embodiment

This embodiment is a method for preparing highly concentrated liquid bromine-containing solutions using elemental bromine in conjunction with a solid organic or inorganic halogenating agent. The golden colored solutions produced as a result of this method contain 48-62% more available bromine than solutions that are available commercially. The solutions are stabilized to physical and chemical degradation reactions by adjusting the hydroxide ion to hydrogen ion source (sulfamic acid plus $Br_2$) mole ratio to 2.3:1. A typical reaction is described in Example 4. The method resulted in a solution containing 22.9% as $Br_2$ (10.2% as $Cl_2$).

The method preferably includes the following steps. Steps (a)-(g) may be performed sequentially or as otherwise set forth below. Steps (a) and (b) may be performed simultaneously, followed by the remaining steps. Steps (e) and (g) may be combined.

a. Dispersing solid sulfamic acid in an aqueous phase.

Sulfamic acid displays moderate solubility in water (14.7 g/100 g at 0° C.). When the amount of sulfamic acid added to water exceeds the solubility limit at any given temperature, some of the solid remains undissolved. Upon stirring the mixture, the sulfamic acid solids are dispersed in the aqueous phase. Preferably, a slurry of between about 25% to about 75% solid sulfamic acid in water is employed, with about 30% to about 40% being the most preferred range.

b. Forming a solution of the alkali metal or earth alkali metal salt of sulfamic acid in the aqueous phase.

To the stirred dispersion of solid sulfamic acid in water is added an alkaline source in order to form a solution of the alkali metal or earth alkali metal salt of sulfamic acid. Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The amount of 50% NaOH solution employed should preferably be at least sufficient to fully neutralize the sulfamic acid and form sodium sulfamate according to equation (5).

$$NH_2SO_3H + NaOH \rightarrow [NH_2SO_3^-][Na^+] + H_2O \quad (5)$$
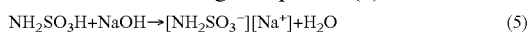

Even more preferably, a molar excess of 50% NaOH is utilized relative to the amount of sulfamic acid. For reasons that will become apparent in steps (c) and (d), about 1.2 to about 1.8 moles of hydroxide ions are introduced for every mole of sulfamic acid present.

If available, solid alkali metal salts of sulfamic acid may be used in the method of this embodiment. In these circumstances, it is only necessary to dissolve the salts in water to make a solution. Preferably, an additional quantity of 50% NaOH is then utilized. For reasons that will become apparent in steps (c) and (d), about 0.2 to about 0.8 moles of hydroxide ions are introduced for every mole of alkali metal salt of sulfamic acid present.

c. Introducing elemental bromine.

The amount of elemental bromine added depends on the amount of sulfamic acid originally present. A mole ratio of about 0.4:1 to about 0.8:1 sulfamic acid to elemental bromine is advantageous to the stability of the final product, with about 0.45:1 to about 0.6:1 being the most preferred mole ratio range.

The elemental bromine is dropped into the reaction mixture from above the surface, or it may be introduced subsurface via a dip tube. When the latter is preferred, the dip tube should be positioned so that the $Br_2$ is introduced to an area of high turbulence, e.g. near the tip of a rotating agitator blade for efficient mixing in the reaction medium. For both subsurface and supersurface addition methods, the $Br_2$ is added with sufficient mixing and at a rate to avoid significant phase separation and pooling at the bottom of the reactor.

With adequate mixing, the $Br_2$ introduced to the reactor containing the solution of sodium hydroxide and sodium sulfamate hydrolyzes readily according to reaction (6).

$$Br_2 + H_2O \rightarrow HOBr + HBr \quad (6)$$

The hypobromous acid formed reacts with sodium sulfamate to form sodium N-bromosulfamate according to reaction (7).

$$HOBr + [NH_2SO_3^-][Na^+] \rightarrow [Br-NHSO_3^-][Na^+] + H_2O \quad (7)$$
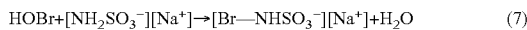

The HBr that is generated in reaction (6) immediately undergoes an acid-base neutralization reaction (8) with the excess sodium hydroxide introduced in step (b).

$$HBr + NaOH \rightarrow NaBr + H_2O \quad (8)$$

When all the excess sodium hydroxide has been consumed by the HBr, additional quantities of base are released from the sodium N-bromosulfamate as follows:

$$[Br-NHSO_3^-][Na^+] + HBr \rightarrow [Br-NHSO_3H] + NaBr \quad (9)$$
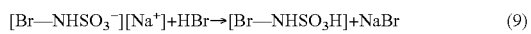

Reactions (8) and (9) are strongly exothermic, so the reaction medium is cooled, preferably to below 85° F., to suppress the degradation of sodium N-bromosulfamate and N-bromosulfamic acid.

Neutralization reactions (8) and (9) demonstrate that as the elemental bromine is introduced, the reaction medium undergoes a pH swing from alkaline to acidic. When the addition of elemental bromine is complete, the pH should be between about 0.5 and about 9, preferably between about 1.0 and about 4.5. These pH conditions facilitate the chemical reaction of step (d).

d. Introducing sufficient solid organic or inorganic halogenating agent to oxidize all or substantially all of the remaining bromide ions into bromine.

Solid inorganic halogenating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing about 65-75% available chlorine) are most preferred.

Solid organic halogenating agents include any organic compound in which one or more halogen atoms such as Cl, Br, or I is present in oxidation state+1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2H$_2$O), potassium dichloroisocyanurate, dichloroisocyanuric acid, trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin. A particularly preferred source of a solid, organic halogenating agent is trichloroisocyanuric acid (TCCA). Preferably this is used as a fine, dry powder. In this form, the TCCA reacts rapidly with the NaBr generated in reactions (8) and (9) according to reaction (10).

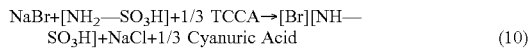

NaBr+[NH$_2$—SO$_3$H]+1/3 TCCA→[Br][NH—SO$_3$H]+NaCl+1/3 Cyanuric Acid    (10)

Although dry powdered TCCA is favored because of its easy handling characteristics, TCCA powdered wetcake may also be employed. The advantage of using TCCA wetcake is that it may be taken directly from the TCCA-producing reactors and so costs associated with drying of the material are eliminated.

When solid organic or inorganic halogenating agents are used in this fashion, all of the Br moieties introduced to the reactor as elemental bromine can materialize as active bromine in the final product. None are wasted as by-product bromide ion salts. Thus, instead of wasting half of the Br moieties as inactive bromide ion, regeneration by, for example, TCCA as described in reaction (10) will ensure that both bromine atoms are utilized as active forms.

e. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic halogenating agent is TCCA, cyanuric acid is a reaction by-product that is insoluble in the reaction medium (see reaction (10)). Filtration of the cyanuric acid (CA) residue is carried out at about pH 1-9, but preferably at about pH 1-6 to maximize its recovery from solution and minimize the amount of bromine vapors that fume from the reaction medium. Upon washing the filtercake with water to remove the mother liquors, a highly pure CA wetcake is recovered. This can be recycled to other processes to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following reaction:

CA+NaOH→NaCA+H$_2$O    (11)

The amount of 50% sodium hydroxide solution employed depends on the amount of solid organic halogenating agent used in step (d). When TCCA is the solid organic halogenating agent, sufficient 50% NaOH solution is introduced slowly with mixing and cooling to convert all or substantially all of the cyanuric acid liberated in reaction (10) into its monosodium salt via reaction (11). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

f. Adding an alkaline source to the reaction mother liquors, such that if the alkaline source is a hydroxide salt, the overall mole ratio of hydroxide ion to sulfamic acid is between about 3:1 and about 5:1, preferably between about 4:1 and about 5:1. This does not include any hydroxide salt that may be used to convert cyanuric acid into its alkali metal or earth alkali metal salt as described in step (e).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The purpose is to deprotonate the bromo derivative of sulfamic acid to form the bromo derivative of sodium sulfamate according to reaction (12).

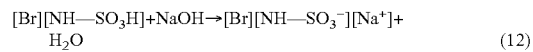

[Br][NH—SO$_3$H]+NaOH→[Br][NH—SO$_3^-$][Na$^+$]+H$_2$O    (12)

g. Removing any further insoluble residues that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation step described in step (e). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di-and trisodium salts display exceptional solubility in ordinary water and are thus useful water treating agents in their own right. However, in comparison to the amount of solids recovered in step (e), the amount of solid that may subsequently develop is relatively low, and step (g) may require only a polishing solid-liquid separation, with, for example, a cartridge filter. Moreover, the two solid-liquid separation steps of (e) and (g) may be combined into a single operation performed at step (e).

EXAMPLE 4

Deionized water (120 ml) was introduced to a 4-necked round bottom flask and solid sulfamic acid (85 g) was added. The slurry was stirred and 50% NaOH (88.2 g) was slowly added as the flask was chilled in an ice bath to keep the temperature of the flask contents at around 75° F. Using a dropping funnel, elemental bromine (58.7 g) was dispensed at a rate of about one drop per second to the reaction medium, also with stirring and cooling to maintain a reaction temperature of 68° F. When the bromine addition was complete, the pH of the reaction medium was measured to be 1.80. A single charge of powdered trichloroisocyanuric acid (90.4% available $Cl_2$) (28.6 g) was then delivered to the reaction medium through one of the necks of the flask. Stirring and cooling was continued as a fine powdery precipitate of cyanuric acid developed. After 10 minutes, 50% NaOH (8 g) was added dropwise in order to diminish the amount of bromine vapors that were fuming from the reaction medium. The cyanuric acid precipitate was then removed by vacuum filtration and the filter cake was washed with two bed volumes of deionized water that were not combined with the mother liquors. The wetcake was placed in an oven set at 125° F. for drying overnight. Using a dropping funnel, additional 50% NaOH (131.8 g) was added to the filtrate, again with cooling and stirring, such that the temperature remained at 74° F. Any solids that precipitated from solution were removed by vacuum filtration immediately upon completing the addition of the 50% NaOH. Iodometric titration of the resultant golden yellow filtrate yielded a bromine content of 22.9% as $Br_2$ (10.2% as $Cl_2$) which corresponded to a yield of 99.1% (based on the sum of the bromine and TCCA charges). The solution possessed a hydroxide ion to hydrogen ion source (sulfamic acid plus $Br_2$) mole ratio of 2.3:1.

The Third Embodiment

The third embodiment is a method for preparing a highly concentrated mixed halogen solution that contains both bromine and chlorine. The method utilizes elemental bromine in conjunction with a solid organic or inorganic chlorinating agent. This light golden-colored composition contains 46-60% more available halogen than the all-bromine solutions that are currently available commercially. A typical reaction is described in Example 6. The method resulted in a solution containing a total halogen content of 22.4% when expressed as $Br_2$ (10.1% when expressed as $Cl_2$).

A major benefit of a mixed halogen biocide is in the treatment of contaminated water that exerts a considerable halogen demand. This chemical demand can be satisfied by the less expensive chlorine portion of the composition, permitting more of the bromine portion to be available for microbiological control. Mixed halogen compositions are also safer and more convenient to manufacture than those that are predominantly bromine-based. For example, during the preparation of the latter, the solutions have a tendency to emit deep red, highly corrosive and toxic bromine fumes right up until the final addition of the alkaline source. These vapors must be scrubbed from the reaction vessel's headspace in order to eliminate atmospheric release, worker exposure, and to prevent the fumes from entering and damaging expensive vacuum processing equipment. By contrast, the mixed halogen compositions emit hardly any deep red bromine fumes during their manufacture. Thus, the necessity for scrubbing the reaction vessel's headspace is eliminated.

A further significant aspect of compositions based on mixtures of stabilized bromine and chlorine is that in water systems employing long contact times, there may be sufficient time for the N-chlorosulfamate to react with "spent" bromide ion and regenerate N-bromosulfamate according to the following reaction.

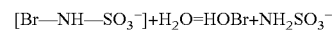
[Br—NH—$SO_3^-$]+$H_2O$=HOBr+$NH_2SO_3^-$

Upon performing biocidal and oxidative reactions, HOBr reverts to soluble bromide ion. This can enter into reaction with N-chlorosulfamate to generate additional N-bromosulfamate.

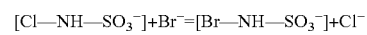
[Cl—NH—$SO_3^-$]+$Br^-$=[Br—NH—$SO_3^-$]+$Cl^-$

In this way, the consumer is able to derive the performance benefits of two moles of N-bromosulfamate for the price of one mole of N-bromosulfamate and one mole of N-chlorosulfamate.

Generally, chlorinated compounds display higher water solubility than their brominated counterparts. Further, a mixed halogen composition may be formulated to employ far less sodium bromide salt than an all-bromine solution. Thus, another highly advantageous facet of this invention is that it makes possible the formation of a mixed halogen composition that is lower in solids and is inherently more soluble than those based solely on bromine. This highly water-soluble composition exhibits improved physical stability as it becomes less prone to solid precipitation on storage.

The method preferably includes the following steps. Steps (a)-(g) may be performed sequentially or as otherwise set forth below. Steps (a) and (b) may be performed simultaneously, followed by the remaining steps. Steps (e) and (g) may be combined.

a. Dispersing solid sulfamic acid in an aqueous phase.

Sulfamic acid displays only moderate solubility in water (14.7 g/100 g at 0° C.). When the amount of sulfamic acid added to water exceeds the solubility limit at any given temperature some of the solid remains undissolved. Upon stirring the mixture, the sulfamic acid solids are dispersed in the aqueous phase. Preferably, a slurry of between about 25% to about 75% solid sulfamic acid in water is employed, with about 30% to about 40% being the most preferred range.

b. Forming a solution of the alkali metal or earth alkali metal salt of sulfamic acid in the aqueous phase.

To the stirred dispersion of solid sulfamic acid in water is added an alkaline source in order to form a solution of the alkali metal or earth alkali metal salt of sulfamic acid. Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The amount of 50% NaOH solution employed should preferably be at least sufficient to fully neutralize the sulfamic acid and form sodium sulfamate according to equation (13).

$$NH_2SO_3H + NaOH \rightarrow [NH_2SO_3^-][Na^+] + H_2O \quad (13)$$

Even more preferably, a molar excess of 50% NaOH is utilized relative to the amount of sulfamic acid. For reasons that will become apparent in steps (c) and (d), about 1.2 to about 1.8 moles of hydroxide ions are introduced for every mole of sulfamic acid present.

If available, solid alkali metal salts of sulfamic acid may be used in the method of this embodiment. In these circumstances it is only necessary to dissolve the salts in water to make a solution. Preferably, an additional quantity of 50% NaOH is then utilized. For reasons that will become apparent in steps (c) and (d), about 0.2 to about 0.8 moles of hydroxide ions are introduced for every mole of alkali metal salt of sulfamic acid present.

c. Introducing elemental bromine.

The amount of elemental bromine added depends on the mole ratio of bromine to chlorine that is desired in the final product, and the amount of sulfamic acid used in step (a). For example, a mixed halogen composition containing 80 mole % bromine and 20 mole % chlorine is prepared using 0.66 moles of bromine per mole of available chlorine provided by the solid chlorinating agent used in step (d). A mole ratio of about 0.75:1 to about 1.5:1 sulfamic acid to available halogen provided by the sum of the bromine and the solid chlorinating agent is advantageous to the stability of the final product, with about 0.95:1 to about 1.2:1 being the most preferred mole ratio range.

The elemental bromine is dropped into the reaction mixture from above the surface, or it may be introduced subsurface via a dip tube. When the latter is preferred, the dip tube should be positioned so that the $Br_2$ is introduced to an area of high turbulence, e.g. near the tip of a rotating agitator blade for efficient mixing in the reaction medium. For both subsurface and supersurface addition methods, the $Br_2$ is added with sufficient mixing and at a rate to avoid significant phase separation and pooling at the bottom of the reactor.

With adequate mixing, the $Br_2$ introduced to the reactor containing the solution of sodium hydroxide and sodium sulfamate hydrolyzes readily according to reaction (14).

$$Br_2 + H_2O \rightarrow HOBr + HBr \quad (14)$$

The hypobromous acid formed reacts with sodium sulfamate to form sodium N-bromosulfamate according to reaction (15).

$$HOBr + [NH_2SO_3^-][Na^+] \rightarrow [Br-NHSO_3^-][Na^+] + H_2O \quad (15)$$

The HBr that is generated in reaction (14) immediately undergoes an acid-base neutralization reaction (16) with the excess sodium hydroxide introduced in step (b).

$$HBr + NaOH \rightarrow NaBr + H_2O \quad (16)$$

When all the excess sodium hydroxide has been consumed by the HBr, additional quantities of base are released from the sodium N-bromosulfamate as follows:

$$[Br-NHSO_3^-][Na^+] + HBr \rightarrow [Br-NHSO_3H] + NaBr \quad (17)$$

Reactions (16) and (17) are strongly exothermic, so the reaction medium is cooled, preferably to below 85° F., to suppress the degradation of sodium N-bromosulfamate and N-bromosulfamic acid.

Neutralization reactions (16) and (17) demonstrate that as the elemental bromine is introduced, the reaction medium undergoes a pH swing from alkaline to acidic conditions.

When the addition of elemental bromine is complete, the pH is between about 0.5 and about 9, preferably between about 1.0 and about 4.5. These pH conditions facilitate the chemical reaction of step (d).

d. Introducing sufficient solid organic or inorganic chlorinating agent to oxidize all or substantially all of the remaining bromide ions into bromine, and to release soluble chlorine into the solution by complexing with sulfamic acid.

Solid inorganic chlorinating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing about 65-75% available chlorine) are most preferred.

Solid organic chlorinating agents include any organic compound in which one or more chlorine atoms is present in oxidation state+1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2H$_2$O), potassium dichloroisocyanurate, dichloroisocyanuric acid, trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin. A particularly preferred source of a solid, organic chlorinating agent is trichloroisocyanuric acid (TCCA). Preferably this is used as a fine, dry powder.

The solid chlorinating agent has two functions. First, it oxidizes all of the bromide ions released in reactions (16) and (17) into bromine which reacts with the sulfamic acid to form N-bromosulfamic acid. When the solid chlorinating agent is TCCA, it reacts as indicated in reaction (18).

$$NaBr + [NH_2-SO_3H] + 1/3 \text{ TCCA} \rightarrow$$
$$[Br][NH-SO_3H] + NaCl + 1/3 \text{ Cyanuric Acid} \quad (18)$$

Second, the excess solid chlorinating agent releases soluble chlorine into the aqueous solution by complexing with sulfamic acid to form N-chlorosulfamic acid. When the solid chlorinating agent is TCCA, it reacts according to reaction (19).

$$NH_2-SO_3H + 1/3 \text{ TCCA} \rightarrow [Cl][NH-SO_3H] + 1/3 \text{ Cyanuric Acid} \quad (19)$$

Although dry powdered TCCA is favored because of its easy handling characteristics, TCCA powdered wetcake may also be employed. The advantage of using TCCA wetcake is that it may be taken directly from the TCCA-producing reactors and so costs associated with drying of the material are eliminated.

When solid organic or inorganic halogenating agents are used in this fashion, all of the Br moieties introduced to the reactor as elemental bromine can materialize as active bromine in the final product. None are wasted as by-product bromide ion salts. Thus, instead of wasting half of the Br moieties as inactive bromide ion, regeneration by, for example, TCCA as described in reaction (18) will ensure that both bromine atoms are utilized as active forms.

e. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic chlorinating agent is TCCA, cyanuric acid is a reaction by-product that is insoluble in the reaction medium (see reactions (18) and (19)). Filtration of the cyanuric acid (CA) residue is carried out at about pH 1-9, but preferably at about pH 1-6 to maximize its recovery from solution and minimize the amount of bromine vapors that fume from the reaction medium. Upon washing the filtercake with water to remove the mother liquors, a highly pure CA wetcake is recovered. This can be recycled to other processes to make additional quantities of TCCA, NADCC, or $NaDCC.2H_2O$ that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following reaction:

$$CA + NaOH \rightarrow NaCA + H_2O \quad (20)$$

The amount of 50% sodium hydroxide solution employed depends on the amount of solid organic chlorinating agent used in step (d). When TCCA is the solid organic chlorinating agent, sufficient 50% NaOH solution is introduced slowly with mixing and cooling to convert all or substantially all of the cyanuric acid liberated in equations (18) and (19) into its monosodium salt via reaction (20). Monosodium cyanurate is insoluble in the reaction medium at pH<9. As is true of cyanuric acid, monosodium cyanurate can be separated and recycled to other processes in order to make additional quantities of TCCA, NADCC, or $NaDCC.2H_2O$ that can be used in the method of the current invention. This is accomplished by performing a solid-liquid separation, as described above, which is done when the pH stabilizes at about 9.

f. Adding an alkaline source to the reaction mother liquors, such that if the alkaline source is a hydroxide salt, the overall mole ratio of hydroxide ion to sulfamic acid is between about 3:1 and about 5:1, preferably between about 4:1 and about 5:1. This does not include any hydroxide salt that may be used to convert cyanuric acid into its alkali metal or earth alkali metal salt as described in step (e).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The purpose is to deprotonate the bromo derivative of sulfamic acid to form the bromo derivative of sodium sulfamate according to reaction (21).

$$[Br][NH-SO_3H] + NaOH \rightarrow [Br][NH-SO_3^-][Na^+] + H_2O \quad (21)$$

g. Removing any further insoluble residues that develop with a conventional solid-liquid separation technique.

As noted above, any suitable solid-liquid separation technique may be employed. Generally, when TCCA is the chlorinating agent, almost 90% of CA reaction by-product is recovered as a highly pure wetcake in the first solid-liquid separation step described in step (e). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di- and trisodium salts display exceptional solubility in ordinary water and are thus useful water treating agents in their own right. However, in comparison to the amount of solids recovered in step (e), the amount of solid that may subsequently develop is relatively low, and step (g) may require only a polishing solid-liquid separation, with, for example, a cartridge filter. Moreover, the two solid-liquid separation steps of (e) and (g) may be combined into a single operation performed at step (e).

EXAMPLE 5

This example describes the preparation of a mixed halogen solution that was formulated to contain a theoretical 80 mole % bromine and 20 mole % chlorine.

Deionized water (138.2 ml) was introduced to a four-necked round bottom flask and solid sulfamic acid (85.0 g) was added. The slurry was stirred and 50% NaOH (89.0 g) was slowly added as the flask was chilled in an ice bath to keep the temperature of the flask contents at around 74° F. When the addition was complete, the pH of the solution was measured to be 13.2. Using a dropping funnel, elemental bromine (46.8 g) was dispensed at a rate of about one drop per second to the reaction medium, also with stirring and cooling to maintain a reaction temperature of less than 68° F. When the bromine addition was complete, the pH of the reaction medium was measured to be 2.16. A single charge of powdered trichloroisocyanuric acid (90.4% available $Cl_2$) (34.6 g) was then delivered to the reaction medium through one of the necks of the flask. Stirring and cooling continued as normal as a fine powdery precipitate of cyanuric acid developed. After 10 minutes, the headspace in the reactor became devoid of the dark red bromine fumes that are apparent when making the all-bromine solution described in Example 2. After that, the cyanuric acid precipitate was then removed by vacuum filtration and the filter cake was washed with two bed volumes of deionized water that were not combined with the mother liquors. The wetcake was placed in an oven set at 125° F. for drying overnight. Using a dropping funnel, additional 50% NaOH (126.8 g) was added to the filtrate, again with cooling and stirring, such that the temperature remained at 74° F. Any solids that precipitated from solution were removed by vacuum filtration immediately upon completing the addition of the 50% NaOH. Iodometric titration of the resultant golden yellow filtrate yielded a solution with a total halogen content of 22% when expressed as $Br_2$ (10.1% when expressed as $Cl_2$) which corresponded to a yield of 97.2% based on the sum of the bromine and TCCA charges to the reactor. The solution possessed a hydroxide ion to hydrogen ion source (sulfamic acid plus $Br_2$) mole ratio of 2.3:1. The weight of the dry solids removed in the first filtration indicated that 92.2% of the cyanuric acid had been recovered.

The Fourth Embodiment.

The fourth embodiment is a method of preparing highly water soluble, bromine-containing solid compounds, namely, the alkali metal or earth alkali metal salt of hydrated N-bromosulfamate and the alkali metal or earth alkali metal salt of anhydrous N-bromosulfamate. The method uses elemental Br$_2$ in conjunction with a solid organic or inorganic halogenating agent under reaction conditions designed to promote the formation of the solid, e.g. above the solubility limit. The solubility of the sodium salt of hydrated N-bromosulfamate in the reaction medium of this embodiment is about 23.6% as Br$_2$ (10.6% as Cl$_2$). In order to exceed this solubility limit, the sum of the elemental Br$_2$ and organic or inorganic halogenating agent charges to the reactor are adjusted accordingly. A typical reaction is described in Example 6. Initially the method resulted in a supersaturated solution containing 26.1% as Br$_2$ (11.63% as Cl$_2$). Crystallization of the solid product was initiated by chilling the reaction medium.

A unique aspect of this method is that it can be used to yield three different useful products. The first is the solid alkali metal or earth alkali metal salt of hydrated N-bromosulfamate in equilibrium with its saturated solution. The solid need not be isolated from the saturated solution. Instead, the combination product, a slurry, may be advantageously packaged and transported to a separate location for subsequent reconstitution by simple addition of water to yield an aqueous stabilized, liquid bromine composition whose concentration can be tailored to the amount of reconstitution water used. The second and third products are the solid alkali metal or earth alkali metal salt of hydrated N-bromosulfamate and the solid alkali metal or earth alkali metal salt of anhydrous N-bromosulfamate, respectively. These high-activity solids are stable and dissolve rapidly and completely to yield a highly concentrated bromine containing solution.

The method preferably includes the following steps. Steps (a)-(h) or (a)-(i) may be performed sequentially or as otherwise set forth below. Steps (a) and (b) may be performed simultaneously, followed by the remaining steps. Steps (e) and (g) may be combined.

a. Dispersing solid sulfamic acid in an aqueous phase.

Sulfamic acid displays only moderate solubility in water (14.7 g/100 g at 0° C.). When the amount of sulfamic acid added to water exceed the solubility limit at any given temperature some of the solid remains undissolved. Upon stirring the mixture, the sulfamic acid solids are dispersed in the aqueous phase. Preferably, solid sulfamic acid is slurried into ¼ to ¾ its weight of water, with about ½ its weight of water being especially preferred.

b. Forming a solution of the alkali metal or earth alkali metal salt of sulfamic acid in the aqueous phase.

To the stirred dispersion of solid sulfamic acid in water is added an alkaline source in order to form a solution of the alkali metal or earth alkali metal salt of sulfamic acid. Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The amount of 50% NaOH solution employed should preferably be at least sufficient to fully neutralize the sulfamic acid and form sodium sulfamate according to equation (22).

$$NH_2SO_3H + NaOH \rightarrow [NH_2SO_3^-][Na^+] + H_2O \qquad (22)$$

Even more preferably, a molar excess of 50% NaOH is utilized relative to the amount of sulfamic acid. For reasons that will become apparent in steps (c) and (d), about 1.2 to about 1.8 moles of hydroxide ions are introduced for every mole of sulfamic acid present.

If available, solid alkali metal salts of sulfamic acid may be used in the method of this embodiment. In these circumstances, it is only necessary to dissolve the salts in water to make a solution. Preferably, an additional quantity of 50% NaOH is then utilized. For reasons that will become apparent in steps (c) and (d), about 0.2 to about 0.8 moles of hydroxide ions are introduced for every mole of alkali metal salt of sulfamic acid present.

c. Introducing elemental bromine.

The amount of elemental bromine added depends on the amount of sulfamic acid originally present. A mole ratio of about 0.4:1 to about 0.8:1 sulfamic acid to elemental bromine is advantageous to the stability of the final product, with about 0.45:1 to about 0.6:1 being the most preferred mole ratio range.

The elemental bromine is dropped into the reaction mixture from above the surface, or it may be introduced subsurface via a dip tube. When the latter is preferred, the dip tube should be positioned so that the Br$_2$ is introduced to an area of high turbulence, e.g. near the tip of a rotating agitator blade for efficient mixing in the reaction medium. For both subsurface and supersurface addition methods, the Br$_2$ is added with sufficient mixing and at a rate to avoid significant phase separation and pooling at the bottom of the reactor.

With adequate mixing, the Br$_2$ introduced to the reactor containing the solution of sodium hydroxide and sodium sulfamate hydrolyzes readily according to reaction (23).

$$Br_2 + H_2O \rightarrow HOBr + HBr \qquad (23)$$

The hypobromous acid formed reacts with sodium sulfamate to form sodium N-bromosulfamate according to reaction (24).

$$HOBr + [NH_2SO_3^-][Na^+] \rightarrow [Br-NHSO_3^-][Na^+] + H_2O \qquad (24)$$

The HBr that is generated in reaction (23) immediately undergoes an acid-base neutralization reaction (25) with the excess sodium hydroxide introduced in step (b).

$$HBr + NaOH \rightarrow NaBr + H_2O \qquad (25)$$

When all the excess sodium hydroxide has been consumed by the HBr, additional quantities of base are released from the sodium N-bromosulfamate as follows:

$$[Br-NHSO_3^-][Na^+] + HBr \rightarrow [Br-NHSO_3H] + NaBr \qquad (26)$$

Reactions (25) and (26) are strongly exothermic and so the reaction medium is cooled, preferably to below 85° F. to suppress the degradation of sodium N-bromosulfamate and N-bromosulfamic acid.

Neutralization reactions (25) and (26) demonstrate that as the elemental bromine is introduced, the reaction medium undergoes a pH swing from alkaline to acidic conditions. When the addition of elemental bromine is complete, the pH is between about 0.5 and about 9, preferably between about 1.0 and about 4.5. These pH conditions facilitate the chemical reaction of step (d).

d. Introducing sufficient solid organic or inorganic halogenating agent to oxidize all or substantially all of the remaining bromide ions into bromine.

Solid inorganic halogenating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing about 65-75% available chlorine) are most preferred.

Solid organic halogenating agents include any organic compound in which one or more halogen atoms such as Cl, Br, or I is present in oxidation state+1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2H$_2$O), potassium dichloroisocyanurate, dichloroisocyanuric acid, trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin. A particularly preferred source of a solid, organic halogenating agent is trichloroisocyanuric acid (TCCA). Preferably this is used as a fine, dry powder. In this form, the TCCA reacts rapidly with the NaBr generated in reactions (25) and (26) according to reaction (27).

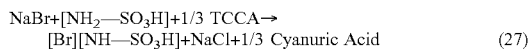
NaBr+[NH$_2$—SO$_3$H]+1/3 TCCA→
[Br][NH—SO$_3$H]+NaCl+1/3 Cyanuric Acid   (27)

Although dry powdered TCCA is favored because of its easy handling characteristics, TCCA powdered wetcake may also be employed. The advantage of using TCCA wetcake is that it may be taken directly from the TCCA-producing reactors and so costs associated with drying of the material are eliminated.

When solid organic or inorganic halogenating agents are used in this fashion, all of the Br moieties introduced to the reactor as elemental bromine can materialize as active bromine in the final product. None are wasted as by-product bromide ion salts. Thus, instead of wasting half of the Br moieties as inactive bromide ion, regeneration by, for example, TCCA as described in reaction (27) will ensure that both bromine atoms are utilized as active forms.

e. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic halogenating agent is TCCA, cyanuric acid is a reaction by-product that is insoluble in the reaction medium (see reaction (27)). Filtration of the cyanuric acid (CA) residue is carried out at about pH 1-9, but preferably at about pH 1-6 to maximize its recovery from solution and minimize the amount of bromine vapors that fume from the reaction medium. Upon washing the filter-cake with water to remove the mother liquors, a highly pure CA wetcake is recovered. This can be recycled to other processes to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following reaction:

CA+NaOH→NaCA+H$_2$O   (28)

The amount of 50% sodium hydroxide solution employed depends on the amount of solid organic halogenating agent used in step (d). When TCCA is the solid organic halogenating agent, sufficient 50% NaOH solution is introduced slowly with mixing and cooling to convert all or substantially all of the cyanuric acid liberated in reaction (27) into its monosodium salt via reaction (28). Monosodium cyanurate is insoluble in the reaction medium at pH<9. As is true of cyanuric acid, monosodium cyanurate can be separated and recycled to other processes in order to make additional quantities of TCCA, NADCC, or NaDCC.2H$_2$O that can be used in the method of the current invention. This is accomplished by performing a solid-liquid separation, as described above, which is done when the pH stabilizes at about 9.

f. Adding an alkaline source to the reaction mother liquors, such that if the alkaline source is a hydroxide salt, the overall mole ratio of hydroxide ion to sulfamic acid is between about 3:1 and about 5:1, preferably between about 4:1 and about 5:1. This does not include any hydroxide salt that may be used to convert cyanuric acid into its alkali metal or earth alkali metal salt as described in step (e).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, the 50% NaOH solution may be diluted with water and used. The alkaline source is introduced to the reaction medium slowly, with stirring and cooling, such that the temperature preferably does not exceed 85° F. The purpose is to deprotonate the bromo derivative of sulfamic acid to form the bromo derivative of sodium sulfamate according to reaction (29).

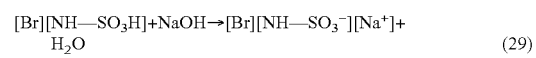
[Br][NH—SO$_3$H]+NaOH→[Br][NH—SO$_3^-$][Na$^+$]+
H$_2$O   (29)

g. Removing any further insoluble residues that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation step described in step (e). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di-and trisodium salts display exceptional solubility in ordinary water and are thus useful water treating agents in their own right. However, in comparison to the amount of solids recovered in step (e), the amount of solid that may subsequently develop is relatively low, and step (g) may require only a polishing solid-liquid separation, with, for example, a cartridge filter. Moreover, the two solid-liquid separation steps of (e) and (g) may be combined into a single operation performed at step (e).

h. Chilling, seeding, evaporating, or otherwise promoting crystallization of the bromine-containing salt from its supersaturated solution.

Crystallization of the bromine-containing solid from its supersaturated solution may be achieved by any conventional means. These methods include, but are not limited to, chilling the reaction medium to reduce the solubility of the bromine-containing salt even further to trigger the precipi-

tation process, seeding the reaction medium with bromine-containing salts obtained in an earlier crop so as to provide a surface on which additional crystals are encouraged to nucleate and grow, and evaporating the reaction medium under vacuum to drive off solvent water and promote the crystallization process.

In certain situations, it may be desirable to conclude the method at this point and leave the alkali metal or earth alkali metal salt of hydrated N-bromosulfamate in equilibrium with its saturated solution. This combination product, a slurry, may be advantageously packaged and transported to a separate location for subsequent reconstitution by simple addition of water to yield an aqueous stabilized liquid bromine-containing composition whose concentration can be tailored to the amount of reconstitution water used.

i. Recovering the resultant solid alkali metal or earth alkali metal salt of hydrated N-bromosulfamate.

Any suitable solid-liquid separation technique can be employed to separate crystals of the alkali metal or earth alkali metal salt of hydrated N-bromosulfamate from the reaction mother liquors. Suitable examples include, but are not limited to, centrifugation, clarification, gravity sedimentation, and vacuum filtration. Filtration is a particularly preferred technique for effecting solid-liquid separation. The solid recovered is the alkali metal or earth alkali metal salt of hydrated N-bromosulfamate as a crystalline material.

In order to obtain the alkali metal or earth alkali metal salt of anhydrous N-bromosulfamate, the hydrated solid must be dried. Any suitable drying technique may be employed to dry the solid. Suitable examples include, but are not limited to, fluidized bed drying, vacuum oven drying, flash drying, and drying over dessicant, such as molecular sieves. Upon dehydration, the solid that is recovered is the alkali metal or earth alkali metal salt of anhydrous N-bromosulfamate.

EXAMPLE 6

Deionized water (50.5 ml) was introduced to a four-necked round bottom flask and solid sulfamic acid (98.3 g) was added. The slurry was stirred and 50% NaOH (102.7 g) was slowly added as the flask was chilled in an ice bath to keep the temperature of the flask contents at around 75° F. Using a dropping funnel, elemental bromine (67.3 g) was dispensed at a rate of about one drop per second to the reaction medium, also with stirring and cooling to maintain a reaction temperature of 68° F. When the bromine addition was complete, the pH of the reaction medium was measured to be 1.97. A single charge of powdered trichloroisocyanuric acid (90.4% available $Cl_2$) (33.1 g) was then delivered to the reaction medium through one of the necks of the flask. Stirring and cooling continued as normal as a fine powdery precipitate of cyanuric acid developed. After 10 minutes, 50% NaOH (11 g) was added dropwise in order to diminish the amount of bromine vapors that were fuming from the reaction medium. The cyanuric acid precipitate was then removed by vacuum filtration. Using a dropping funnel, additional 50% NaOH (161.7 g) was added to the filtrate, again with cooling and stirring, such that the temperature remained at 74° F. Any solids that precipitated from solution were removed by vacuum filtration immediately upon completing the addition of the 50% NaOH. Iodometric titration of the resultant golden yellow filtrate yielded a bromine content of 26.1% as $Br_2$ (11.63% as $Cl_2$) that corresponded to a yield of 98.2% based on the sum of the bromine and TCCA charges to the reaction flask. The slurry possessed a hydroxide ion to hydrogen ion source (sulfamic acid plus $Br_2$) mole ratio of 2.3:1. The solution was poured out of the reaction flask and into a wide-mouth glass jar. This was placed overnight in a refrigerator set to a temperature 60° F. The following morning, the sample had still not crystallized and so the blade of a spatula was used to scrape the inside of the glass jar containing the solution. The sample was placed back into the refrigerator and examined about 8 hours later. A large crystal mass had started to form. The supernatant liquid above the crystals analyzed as 22.7% as $Br_2$ (10.1% as $Cl_2$), indicating the aqueous phase was losing active ingredient at the expense of crystal growth. Overnight, the crystal mass had continued to visibly increase in size, and the supernatant liquid now contained only 16.3% as $Br_2$ (7.25% as $Cl_2$). Upon decanting the supernatant from the crystalline mass, it was found that 42% of the original weight of the solution had turned solid. The crystalline mass was observed to comprise mainly regular rhombohedral crystals of hydrated sodium N-bromosulfamate that possessed a yellow glass-like appearance. A portion of the crystalline mass was lightly dabbed with a paper towel to remove the mother liquors and a weighed amount of this was dissolved in water. It dissolved rapidly and completely. Iodometric titration of the solution was used to calculate that the crystalline solid contained 42.7% as $Br_2$ (18.9% as $Cl_2$).

The invention has been described above with reference to the preferred embodiments. Those skilled in the art may envision other embodiments and variations of the invention that fall within the scope of the claims.

We claim:

1. A method of preparing a bromine-containing liquid, comprising:
    (a) combining solid sulfamic acid, water, and an alkaline source to form a solution of the salt of sulfamic acid, wherein said alkaline source is selected from the group consisting of alkali metal hydroxide and earth alkali metal hydroxide;
    (b) adding a bromine source to said solution, wherein said bromine source is selected from the group consisting of bromine chloride and elemental bromine; and
    (c) forming a bromine-containing liquid, wherein the amounts of said solid sulfamic acid, water, alkaline source, and bromine source are such that said bromine-containing liquid has an active ingredient concentration of greater than 18% as bromine or 8% expressed as chlorine, and further, wherein said bromine-containing liquid has a mole ratio of hydroxide ion to hydrogen ion source of 2.0:1 to 2.86:1.

2. The method of claim 1, wherein in step (a), said solid sulfamic acid is first dispersed in said water, followed by the addition of said alkaline source.

3. The method according to claims 1 or 2, further comprising, after the addition of said bromine source in step (b), adding a second alkaline source, wherein said alkaline source is selected from the group consisting of alkali metal hydroxide and earth alkali metal hydroxide.

4. The method according to claims 1 or 2, further comprising, simultaneously with the addition of said bromine source in step (b), adding a second alkaline source, wherein said alkaline source is selected from the group consisting of alkali metal hydroxide and earth alkali metal hydroxide.

5. The method of claim 1, wherein said bromine-containing liquid retains at least 75% of its active ingredient after storage at 125° F. for at least 31 days.

6. A bromine-containing liquid having an active ingredient concentration of greater than 18% as bromine or 8% expressed as chlorine, made in accordance with the method of claim 1.

7. The bromine-containing liquid of claim 6, wherein said bromine-containing liquid retains at least 75% of its active ingredient after storage at 125° F. for at least 31 days.

8. A method of preparing a bromine-containing liquid, comprising:
(a) combining solid sulfamic acid, water, and a first alkaline source to form a solution of the salt of sulfamic acid, wherein said alkaline source is selected from the group consisting of alkali metal hydroxide and earth alkali metal hydroxide;
(b) adding elemental bromine to said solution;
(c) adding a solid halogenating agent to said solution;
(d) conducting a solid-liquid separation;
(e) adding a second alkaline source, wherein said alkaline source is selected from the group consisting of alkali metal hydroxide and earth alkali metal hydroxide; and
(f) forming a bromine-containing liquid, wherein the amounts of said solid sulfamic acid, water, first and second alkaline sources, and elemental bromine are such that said bromine-containing liquid has an active ingredient concentration of greater than 18% as bromine or 8% expressed as chlorine, and further, wherein said bromine-containing liquid has a mole ratio of hydroxide ion to hydrogen ion source of 2.0:1 to 2.86:1.

9. The method of claim 8, further comprising after step (e), conducting a second solid-liquid separation.

10. The method of claim 8, wherein the mole ratio of hydroxide ion to sulfamic acid is between about 1.2:1 and about 1.8:1.

11. The method of claim 8, wherein in step (a), said solid sulfamic acid is first dispersed in said water, followed by the addition of said first alkaline source.

12. The method of claim 8, wherein in step (b), the amount of elemental bromine added is such that the mole ratio of said sulfamic acid to said elemental bromine is between about 0.4:1 and about 0.8:1.

13. The method according to claims 8 or 11, wherein said solid halogenating agent is an organic halogenating agent.

14. The method of claim 13, wherein said organic halogenating agent is selected from the group consisting of trichloroisocyanuric acid, sodium dichloroisocyanurate, sodium dichloroisocyanurate dihydrate, potassium dichloroisocyanurate, dichloroisocyanuric acid, trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin.

15. The method according to claims 8 or 11, wherein said solid halogenating agent is an inorganic halogenating agent.

16. The method of claim 15, wherein said inorganic halogenating agent is selected from the group consisting of lithium hypochlorite, calcium hypochlorite, and magnesium hypochlorite.

17. A bromine-containing liquid having an active ingredient concentration of greater than 18% as bromine or 8% expressed as chlorine, made in accordance with the method of claim 8.

* * * * *